United States Patent [19]

Sablotsky et al.

[11] Patent Number: 5,032,207
[45] Date of Patent: Jul. 16, 1991

[54] ONE-STEP METHOD FOR FORMING A PRESSURE-SENSITIVE ADHESIVE TRANSDERMAL DRUG DEVICE

[75] Inventors: Steven Sablotsky; Ronald E. LaPrade, both of Miami, Fla.

[73] Assignee: Noven Pharmaceuticals, Inc., Miami, Fla.

[21] Appl. No.: 407,874

[22] Filed: Sep. 15, 1989

Related U.S. Application Data

[63] Continuation-in-part of Ser. No. 295,847, Jan. 11, 1989, which is a continuation-in-part of Ser. No. 164,482, Mar. 4, 1989, Pat. No. 4,816,168.

[51] Int. Cl.⁵ .............................................. B32B 31/18
[52] U.S. Cl. .................................... 156/250; 156/268; 156/510; 83/861; 83/862
[58] Field of Search ............... 156/248, 257, 261, 263, 156/267, 268, 270, 510, 528, 581, 250; 428/40, 41; 83/52, 620, 621, 861, 862; 128/156, 641, 798; 604/304, 307

[56] References Cited

U.S. PATENT DOCUMENTS

| | | |
|---|---|---|
| 360,674 | 4/1887 | Fiske . |
| 1,131,431 | 3/1915 | Smith . |
| 1,963,393 | 6/1934 | Woodall .............................. 156/257 |
| 2,114,411 | 4/1938 | Wesselman . |
| 2,223,828 | 12/1940 | Larson . |
| 2,552,353 | 5/1951 | Troth et al. . |
| 2,977,901 | 4/1961 | Deary, Sr. et al. . |
| 3,006,793 | 10/1961 | Wheeler . |
| 3,020,186 | 2/1962 | Lawrence . |
| 3,469,488 | 9/1969 | Gaspari . |
| 3,786,732 | 1/1974 | Forbes ................................... 83/862 |
| 3,977,310 | 8/1976 | Keck et al. . |
| 4,080,878 | 3/1978 | Gallagher et al. . |

Primary Examiner—Caleb Weston
Attorney, Agent, or Firm—Sybil Meloy

[57] ABSTRACT

A one step method and apparatus for forming a pressure sensitive adhesive transdermal drug device having a scored release liner which comprises positioning a web containing the release liner using a cutting die having a first cutting element designed to completely cut through the web to form the device and a second cutting element designed to cut only the release liner.

1 Claim, 2 Drawing Sheets

ONE-STEP METHOD FOR FORMING A PRESSURE-SENSITIVE ADHESIVE TRANSDERMAL DRUG DEVICE

CROSS-REFERENCE TO RELATED APPLICATION

This application is a continuation-in-part of U.S. Patent Application Ser. No. 295,847 filed Jan. 11, 1989, which was in turn a continuation-in part of U.S. Pat. Application Ser. No. 164,482 filed Mar. 4, 1989, now U.S. Pat. No. 4,816,168 granted Mar. 21, 1989, both of which applications are hereby incorporated by reference.

BACKGROUND OF THE INVENTION

The present invention relates to drug-containing pressure sensitive adhesive containing on one side, a backing, and on the other side, a release liner, (sometimes called a transdermal drug delivery device) and more particularly, to a method and apparatus for forming a transdermal drug device and scoring its liner to permit the liner to be easily removed from the adhesive carrying drug in one step.

Many apparatus and methods have been devised for continuously or intermittently scoring a release liner for use with transdermal drug-containing adhesive in order to permit the liner to be easily removed from the device immediately prior to its being used. One such method is to completely cut through the release liner. However, the typical procedure for the preparation of a transdermal drug delivery device is as follows: First, a dilution or suspension of the adhesive containing the drug is poured onto a flexible plastic intended to function as a disposable release liner. Next, a non-releasable backing material is applied over the adhesive. The result is a web containing an adhesive with a backing on one side and a disposable release liner on the other. A shaped device is then formed by a peripheral cutting through all layers of the resulting web. The disposable release liner is then removed and a second, scored release liner is attached to the transdermal adhesive.

Alternatively, the liner can be first scored and assembled with the adhesive and the backing and then the assembly cut to the desired dimensions.

The purpose of the multi-step procedure for applying the backing and the release liner to the adhesive containing the drug is to avoid the problems encountered when a scored release liner is used in processing. If such a completely cut release liner is used prior to coating, the adhesive can pass through the release liner at the score causing equipment problems, cracking, separation and heat damage.

These prior art methods suffer from the disadvantage that the procedure for applying the release liner requires many steps. It thus has a tendency to be more expensive in large scale manufacturing than a procedure which would involve fewer steps.

SUMMARY OF THE INVENTION

The present invention overcomes the difficulties and disadvantages associated with prior art devices by providing a method and device therefor for simultaneously cutting an assembled transdermal device from a web comprising a backing, a drug-containing adhesive and a release liner.

This invention is accomplished by providing cutting devices sized to cut completely through the periphery of the assembled web to form the transdermal device, and also sized to only cut or score the release liner at a position intermediate to the periphery of the device. The intermediate cut does not extend to the adhesive or the non-releasable backing.

These advantages are accomplished by the use of a cutting device having the configuration of the device to be cut with an exterior cutting element sized to form the transdermal device, and the interior cutting element sized to cut only through the release liner.

DETAILED DESCRIPTION OF THE PREFERRED EMBODIMENT

Figure 1:
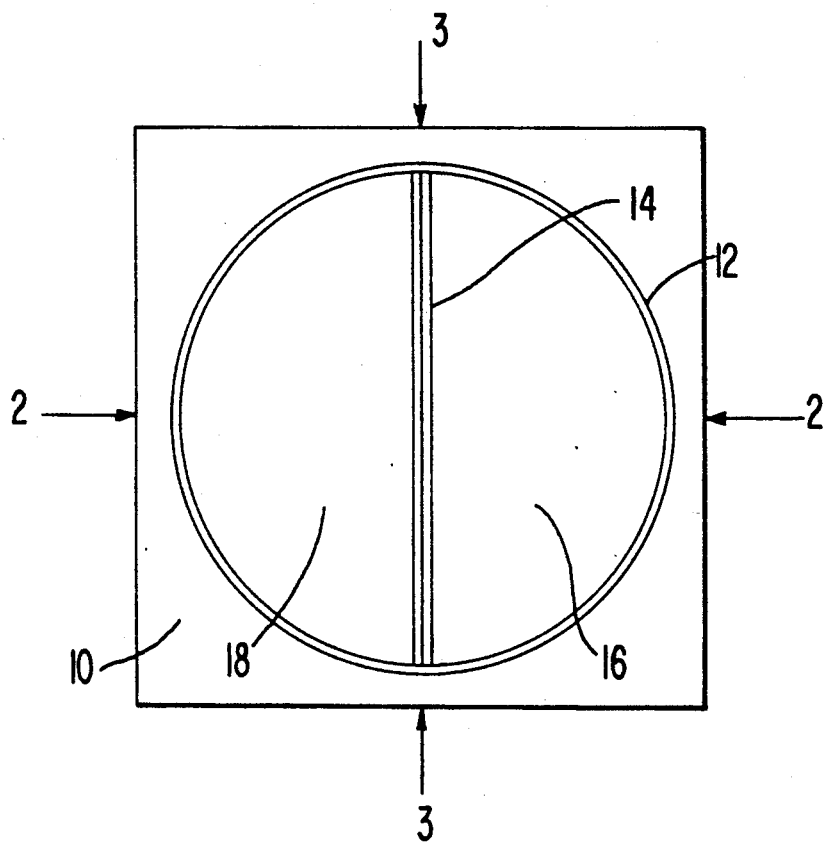
FIG. 1 is a plain view of the device.

The preferred embodiment of the cutting die is illustrated in FIG. 1 in the form a support surface 10 having a two-dimensional cutting element 12 shown as having a generally elliptical configuration with a one-dimensional central cutting element 14 of generally linear shape; and a pair of recesses 16 and 18 formed by the cutting elements 12 and 14. The web of the transdermal bandage is adapted to lay across the rigid support surface shown in FIG. 2 covering the entire well area formed by the cutting element 12. The cutting element 12 is sized with respect to the web so as to completely cut through the web, while the cutting element 14 is sized so as to cut only the release liner. The web is applied with the release liner facing the support.

Figure 2:
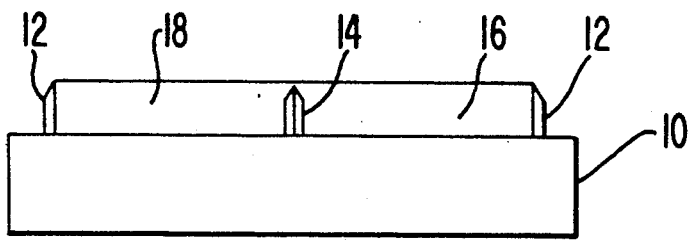
FIG. 2 is a cross section of the device along line 2—2.
Figure 3:
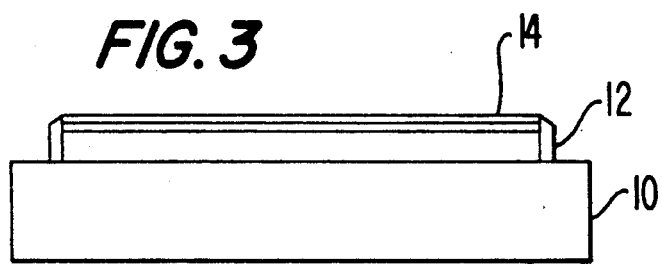
FIG. 3 is a cross section of the device taken along line 3—3.

Referring to FIG. 2, a cross section of the device taken along lines 2—2, the sizing of the cutting elements 12 and 14 is such that the difference in height between cutting element 12 and cutting element 14 is equal to the height of the release liner. Thus, cutting elements 12 and 14 are sized so that cutting element 12 is substantially the height of the web, while cutting element 14 is the height of the transdermal web less the height of all layers other than the release liner.

Figure 4:
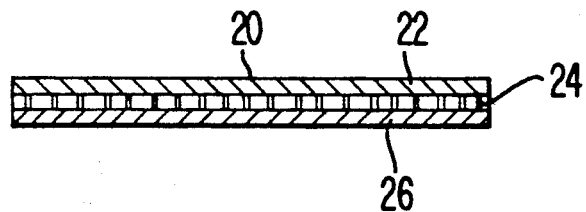
FIG. 4 is a cross-section of the drug delivery device in the web form prior to cutting.

FIG. 4 shows a transdermal web in lateral cross section prior to being cut. Layer 22 is the backing material, layer 24 is the adhesive containing drug and layer 26 is the release liner layer. For purposes of this invention, the release liner layer prior to being cut is available as a web or a continuous roll prepared by applying the fluid adhesive to either the release liner 26 or the backing material 22, then applying either the backing material 22 over release liner 26, respectively, to the other side of the adhesive containing the drug. The stock or web 20 is then placed on the solid support 10 with the release liner 26 facing the cutting elements 12 and 14. The transdermal device is then punched out with a die cooperating with the solid support.

The solid support and the die are preferably made of steel or relatively imcompressible rigid material. It can be machined from a solid member or cast with a generally desired configuration and then machined to the proper dimensions. In any event, the outer cutting element 14 generally has a circumference of from 3 to 40 mm and preferably from 7.9 to 17.7 mm, depending on the surface area needed for delivery of the drug and a radius of 0.48 to 6.4 mm and preferably 1.3 to 2.8 mm, again depending on the appropriate radius for the drug to be delivered, as is known to those skilled in the art.

Any configuration of cutting elements 12 and 14 is possible; however, superior results have been found where cutting element 12 has a single slanted face directed toward the periphery of the template, and cutting element 14 has a dual slant terminating in a central apex.

Cutting elements 12 and 14 are sized so that cutting element, in cooperation with the web, passes completely through the web, while cutting element 14 passes only through the release liner. In general, cutting element 12 is from 100 to 1500 in height, and preferably 900 to 1000, and more preferably, 930 to 950 microns, although obviously the height of the cutting element is dependent upon the height of the web.

Again, the cutting element 14 is preferably 100 to 1500 microns and more preferably 850 to 950 microns and even more preferably 925 to 945 microns, although again the height is totally dependent on the thickness of the release liner. For example, with a stock of 10 microns in thickness where the release liner is 4 microns in thickness, cutting element 12 would 937 in height while cutting element 14 would be 935 microns in height.

Obviously, the cutting element 14 has to extend sufficiently into the release liner to cause a score, but not sufficiently to also cut the adhesive drug-containing layer.

Although the apparatus of this invention can be used with release liners that are as flexible, as more flexible than or equally flexible as the combination of the backing and adhesive layer, it is desirable to use a backing having the same order of frangibility as the release liner, so that the force needed to cut the entire device and at the same time score only the release backing would be about the same.

The foregoing arrangement allows the outside cutting rule to cut complete through all layers of the transdermal device while the center cutting rule only cuts through the release liner. The device further can have the peripheral cutting device extending on one side only toward the periphery, thus permitting straight lines on the interior surface of the cutting element. The dual edge of the intermediate cutting device avoids uncut material in the area. Other variations of the instant device will be apparent to one skilled in the art.

What is claimed is:

1. A method of forming a transdermal drug delivery device having a drug-containing layer, having a scored release liner of one side thereof and having a backing on the other side thereof, said release liner being releasably adherable to said drug-containing layer, said method comprising the steps of:

positioning a web containing said release liner, said drug-containing layer and said backing on a rigid support surface; and cutting said web with a cutting die, said cutting die having a first cutting element with a two-dimensional shape, to cut completely through said web to form a shaped device and having a second linear cutting element interior to the first cutting element, said second cutting element having a one-dimensional shape, and sized to cut only the release liner layer.

* * * * *